United States Patent [19]

Sandvig et al.

[11] Patent Number: 4,888,225

[45] Date of Patent: Dec. 19, 1989

[54] RESIN-IMPREGNATED FOAM MATERIALS AND METHODS

[75] Inventors: Timothy C. Sandvig, Woodville, Wis.; Dennis C. Bartizal; Matthew T. Scholz, both of Woodbury, Minn.; Anthony J. Campagna, Roseville, Minn.; Chris J. Libbey, St. Joseph Township, St. Paul County of St. Croix, Wis.

[73] Assignee: Minnesota Mining and Manufacturing Company, St. Paul, Minn.

[21] Appl. No.: 202,500

[22] Filed: Jun. 3, 1988

Related U.S. Application Data

[63] Continuation-in-part of Ser. No. 15,972, Feb. 18, 1987, which is a continuation-in-part of Ser. No. 784,345, Oct. 4, 1985, Pat. No. 4,683,877.

[51] Int. Cl.[4] .................. A43B 7/32; A43B 13/42; A43B 19/00; A43B 21/06; A61F 5/04
[52] U.S. Cl. ............................ 428/71; 36/88; 36/91; 36/111; 36/44; 36/34 A; 36/34 R; 128/581; 128/586; 128/595; 128/90; 168/12; 168/28; 168/DIG. 1; 206/524.1; 428/305.5; 428/308.4; 428/317.3; 428/317.7; 428/318.6; 428/319.3; 428/423.3; 428/542.8
[58] Field of Search ................ 36/88, 91, 111, 44, 36/34 A, 34 R; 128/581, 586, 595, 90; 168/12, 28, DIG. 1; 206/524.1; 428/305.5, 308.4, 318.6, 319.3, 423.3, 542.8, 913, 317.3, 317.7, 71

[56] References Cited

U.S. PATENT DOCUMENTS

| | | | |
|---|---|---|---|
| 1,914,049 | 6/1933 | Smith | 128/595 |
| 2,759,475 | 8/1956 | Van Swaay | 128/90 |
| 2,800,129 | 7/1957 | Van Swaay | 128/90 |
| 2,973,529 | 3/1961 | Silverman | 128/595 |
| 3,040,740 | 6/1962 | Parker | 128/90 |
| 3,048,169 | 8/1962 | Pierce | 128/90 |
| 3,301,252 | 1/1967 | Mahoney, Jr. | 128/90 |
| 3,320,347 | 5/1967 | Greenawalt | 128/595 |
| 3,373,741 | 3/1968 | Hill et al. | 128/90 |
| 3,375,822 | 4/1968 | Rose | 128/90 |
| 3,572,330 | 3/1971 | Gander | 128/90 |
| 3,608,238 | 9/1971 | Reuter | 47/64 |
| 3,656,475 | 4/1972 | Hanrahan | 128/90 |
| 3,728,206 | 12/1976 | Buese | 161/112 |
| 3,799,755 | 3/1974 | Rack | 47/56 |
| 3,819,796 | 6/1974 | Webster et al. | 264/321 |
| 3,847,722 | 11/1974 | Kistner . | |
| 3,889,417 | 6/1975 | Wood et al. | 47/56 |
| 3,900,024 | 8/1975 | Lauber et al. | 128/91 R |
| 3,935,355 | 1/1976 | Kuhn | 128/90 |
| 3,985,128 | 10/1976 | Garwood et al. | 128/89 |
| 3,998,219 | 12/1976 | Mercer et al. | 128/90 |
| 4,019,506 | 4/1977 | Eschmann | 128/90 |
| 4,060,075 | 11/1977 | Blomer et al. | 128/90 |

(List continued on next page.)

FOREIGN PATENT DOCUMENTS 0223380 5/1987 European Pat. Off. .
8301736 5/1983 World Int. Prop. O. .

Primary Examiner—James C. Cannon
Attorney, Agent, or Firm—Donald M. Sell; Walter N. Kirn; Dale E. Hulse

[57] ABSTRACT

The present invention relates to orthopedic splinting articles and methods for forming orthopedic splints at least part way around an animal body part. The splinting articles comprise a unitary blank formed of an open-celled foam sheet impregnated with a water curable, isocyanate functional, polyurethane prepolymer resin. The blank is dimensioned to extend the length of the body part to be immobilized and to partially, but preferably not completely, extend around the circumference of the body part. Upon activation of the resin impregnated foam sheet and molding the same around the body part, an orthopedic splint is formed. The present invention further relates to the use of such resin-impregnated foam materials as walking heels or laminates betweeen casts and walking heels, as supports for orthotic devices such as arch supports for foot orthotics, and as protective coverings for animal hoofs.

33 Claims, 7 Drawing Sheets

U.S. PATENT DOCUMENTS

| | | | |
|---|---|---|---|
| 4,083,127 | 4/1978 | Hanson | 36/93 |
| 4,144,658 | 3/1979 | Swan, Jr. | 36/117 |
| 4,182,056 | 1/1980 | Dalebout | 36/117 |
| 4,193,395 | 3/1980 | Gruber | 128/90 |
| 4,211,019 | 7/1980 | McCafferty | 36/43 |
| 4,232,457 | 11/1980 | Mosher | 36/44 |
| 4,235,228 | 11/1980 | Gaylord, Jr. et al. | 128/90 |
| 4,245,410 | 1/1981 | Molitor | 36/117 |
| 4,255,202 | 3/1981 | Swan, Jr. | 106/122 |
| 4,280,489 | 7/1981 | Johnson, Jr. | 128/80 H |
| 4,301,564 | 11/1981 | Dalebout | 12/146 R |
| 4,309,990 | 1/1982 | Brooks et al. | 128/91 |
| 4,323,061 | 4/1982 | Usukura | 128/90 |
| 4,325,380 | 4/1982 | Malkin | 128/581 |
| 4,331,134 | 5/1982 | Brooks et al. | 128/90 |
| 4,346,525 | 8/1982 | Larsen et al. | 36/69 |
| 4,347,213 | 8/1982 | Rogers, Jr. | 264/510 |
| 4,370,976 | 2/1983 | Wanchik et al. | 128/77 |
| 4,376,438 | 3/1983 | Straube et al. | 128/90 |
| 4,411,262 | 10/1983 | Von Bonin et al. | 128/90 |
| 4,414,762 | 11/1983 | Salomon et al. | 36/117 |
| 4,419,261 | 12/1983 | Takahashi | 252/182 |
| 4,433,680 | 2/1984 | Yoon | 128/90 |
| 4,439,934 | 4/1984 | Brown | 36/44 |
| 4,442,833 | 4/1984 | Dahlen et al. | 128/90 |
| 4,450,833 | 5/1984 | Brooks et al. | 128/90 |
| 4,451,310 | 5/1984 | Lairloup | 156/78 |
| 4,470,782 | 9/1984 | Zimmerman, Jr. et al. | 425/2 |
| 4,502,479 | 3/1985 | Garwood et al. | 128/90 |
| 4,510,700 | 4/1985 | Brown | 36/44 |
| 4,520,581 | 6/1985 | Irwin et al. | 36/88 |
| 4,522,777 | 6/1985 | Peterson | 264/223 |
| 4,565,250 | 1/1986 | Vasko | 168/12 |
| 4,597,196 | 7/1986 | Brown | 36/44 |
| 4,609,578 | 9/1986 | Reed | 428/76 |
| 4,628,621 | 12/1986 | Brown | 36/44 |
| 4,638,795 | 1/1987 | Richter et al. | |
| 4,667,661 | 5/1987 | Scholz et al. | 128/90 |
| 4,683,877 | 8/1987 | Ersfeld et al. | 428/317.3 |
| 4,705,840 | 11/1987 | Buckanin | 528/53 |

RESIN-IMPREGNATED FOAM MATERIALS AND METHODS

RELATED APPLICATIONS

This application is a continuation-in-part of application Ser. No. 015,972, filed Feb. 18, 1987 for "Orthopedic Splinting Articles and Methods," which application is incorporated herein by reference and which is a continuation-in-part of application Ser. No. 784,345, filed Oct. 4, 1985 for "Orthopedic Casting Article and Method" (now U.S. Pat. No. 4,683,877), which is also incorporated herein by reference.

BACKGROUND

1. The Field of the Invention

The present invention relates to orthopedic splinting materials and methods utilizing an open-celled foam sheet impregnated with a water curable resin. The present invention further relates to the use of such resin-impregnated foam materials as walking heels or laminates between casts and walking heels, as supports for orthotic devices, such as arch supports for foot orthotics, and as protective coverings for animal hoofs.

2. The Prior Art

Severe injury to body limbs, particularly injuries involving a fresh fracture of the bone or damage to the soft tissue supporting the bone, are frequently treated by temporarily immobilizing the injured limb with a splint until the time swelling has abated. After such time, the splint may then be removed and a rigid cast applied. Because a temporary splint must allow for swelling of the limb, the splint generally should not encompass the entire limb so as to better accommodate expansion of the limb. Many different systems have been devised for providing orthopedic splints.

For example, U.S. Pat. Nos. 2,759,475 and 2,800,129 disclose blanks for forming splints comprising a solid thermoplastic material provided on one surface with a foam plastic layer. The blank is heated to a temperature such that the solid thermoplastic material becomes soft, and is then applied to the body part and shaped to form the splint.

Similarly, U.S. Pat. No. 4,442,833 discloses a casting or splinting bandage comprising a closed-cell polymer foam and a plurality of sheets of a textile material impregnated with a water curable resin.

U.S. Pat. No. 4,235,228 discloses an orthopedic material comprising a plaster impregnated fabric core, a layer of padding around at least one surface of the fabric, and a length of tubular stockinet encircling the fabric and padding. This combination can be cut to a desired length, dipped in water to begin hardening of the plaster, attached to a patient by a bandage or other fastener, and allowed to harden to form a splint.

The systems described in U.S. Pat. Nos. 4,442,833 and 4,235,228 are relatively damp when applied, and can thus provide undesirable environments for any wounds present and/or promote skin maceration on those body parts over which the splints are applied.

U.S. Pat. No. 3,985,128 discloses a splint that can be applied dry, but ultraviolet light is required to harden the splint. Thus, such a splint can only be used where a source of ultraviolet light is available. U.S. Pat. No. 3,728,206 describes a foam impregnated with a thermoplastic resin.

U.S. Pat. No. 4,411,262 discloses a constructional material comprising a flexible substrate impregnated or coated with a resin system which is cured by air moisture. In one embodiment, the flexible substrate may be a foam which is resin impregnated by solvent coating onto the foam an isocyanate sump residue which has a viscosity between 3,000 and 50,000 centipoise.

U.S. Pat. No. 4,628,917, which issued on Dec. 16, 1986 and which is assigned to the same assignee as the present invention, discloses a combination of materials that can be used to form a splint or protective covering, including a support mat comprising a flexible fabric impregnated with a water curable resin with a water restricting film along at least one of its major surfaces, and a pressure sensitive adhesive coated padding that can be adhered to the support mat after the fabric is exposed to water so that the resultant laminate can be applied to a person with the dry surface of the padding against the person's skin.

In selecting suitable materials for forming orthopedic splints, the prior art has encountered several problems. First, it has been sought to use a low viscosity resin which may be easily coated upon the supporting fabric or material to be used in the splint. However, splints prepared from such low viscosity resins, when formulated to give a proper set time, typically result in unacceptably high exotherms, which can result in burning the patient. High viscosity resins, on the other hand, typically require complicated techniques for application, such as solvent coating the resin onto the fabric or substrate. Further, the fabrics or scrim materials used in such splints have typically been relatively inextensible in order to provide sufficient strength for the resulting splint; however, the result is a splinting material which has poor extensibility and which thus does not conform well to the body part to which it is applied. Finally, if the splinting materials used in the prior art do not exhibit sufficient water vapor permeability, skin maceration can result.

From the foregoing, it will be appreciated that what is needed in the art is improved orthopedic splinting materials which have acceptable setting times and exotherms without the need for complicated resin application techniques, and which avoid the problems of the prior art set forth above. Such splinting materials and methods for applying such splinting materials are disclosed herein.

Further, in the prior art technologies involving walking heels for casts, foot orthotics, and protective coverings for animal hoofs, problems have arisen due to the irregularities of the surfaces involved. Ideally, it would be desirable to provide a material that would result in an even walking surface for each of these applications, regardless of the irregularity of the surface to which the material is attached. Advantageously, the resin-impregnated foam materials of the present invention serve exceptionally well in these other applications.

BRIEF SUMMARY OF THE INVENTION

The present invention relates to an article which is suitable for forming an orthopedic splint around a portion of an animal body part, which splinting article avoids the problems of the prior art. The article of the present invention greatly simplifies splint application.

According to a presently preferred embodiment of the invention, a unitary blank is provided which comprises a pliant, extensible, and highly conformable substrate. The blank is dimensioned in a first direction sufficient to extend the length of the body part and is dimensioned in a second direction sufficient to extend partially, but preferably not completely, around the circumference of the body part. In this regard, the blank is dimensioned in the second direction so as to envelop the body part to the extent that is needed to support and immobilize the body part, while still accommodating for the swelling which generally occurs as a result of a fresh fracture or soft tissue injury.

Importantly, the blank comprises an open-celled foam sheet and a water curable, isocyanate functional, prepolymer resin impregnated into the open-celled foam sheet. The prepolymer resin is a polyurethane resin formed by reacting a polyisocyanate with a polyol, preferably while the polyisocyanate and the polyol are inside the open-celled foam sheet. The ratio of isocyanate (NCO) groups in the polyisocyanate to hydroxyl (OH) groups in the polyol is about 2:1 to about 3.5:1. The isocyanate equivalent weight in the resultant prepolymer is from about 350 grams to about 1000 grams of prepolymer per isocyanate group. The orthopedic splint is formed by activating the polyurethane prepolymer resin and applying the blank around the portion of the body part to be splinted and immobilized.

The strength and rigidity of the cured splint are dependent primarily upon the rigidity of the cured prepolymer resin rather than the initially flexible open-celled foam sheet. By maintaining the NCO:OH ratio and isocyanate equivalent weight within the ranges disclosed herein, safe levels of heat generated during cure are maintained, while providing a cured resin having the rigidity needed.

Because the polyisocyanate and polyol are preferably not prereacted, but are reacted while within the foam sheet to form the polyurethane prepolymer resin, it is possible to select and employ a prepolymer resin which is more highly viscous than the resins used in the prior art. In this regard, reacting the prepolymer components within the foam sheet itself avoids the necessity of trying to solvent-coat the resultant viscous prepolymer resin or of finding some other method of applying the viscous resin. Surprisingly, the high viscosity prepolymer resins employed in the present invention have good set times, relatively low exotherms, and sufficient rigidity to be useful in supporting an injured body part.

Furthermore, because the foam sheet itself is pliant, extensible, and highly conformable, and because the use of a rigid or stiff scrim which would otherwise impair extensibility is avoided, the extensibility of the resin impregnated foam is quite good. The reason that a rigid scrim is not needed in the present invention is that, surprisingly, the foam sheet alone can be resin loaded to a very high degree and thereby impart the strength necessary to form a suitable orthopedic splint. Also surprisingly, after resin loading the foam sheet to the extent necessary to achieve the desirable degree of strength, the resultant splint still exhibits good water vapor permeability so as to substantially avoid skin maceration.

Because an extra scrim is not needed with the resin impregnated foam sheet, good conformability and moldability and omnidirectional extensibility in applying the splint are made possible. As a result, good alignment of the splint with respect to the body part can be achieved. Another surprising benefit of the present invention is that the surface of the resin impregnated foam sheet is surprisingly less tacky than would be expected (especially at such high resin loadings), thereby greatly facilitating application of the splint.

In summary, the present invention provides a one piece article which may be formed, using solventless techniques, into an orthopedic splint having the following desirable benefits during application: good conformability and moldability, omnidirectional extensibility, good alignment of the splinting material, low exotherm, relatively short cure times, reduced tack, and good resin loading. Upon curing, the resultant splint exhibits good strength and good water vapor permeability.

These and other objects and features of the present invention will become more fully apparent from the following description and appended claims, taken in conjunction with the accompanying drawings.

As will be discussed in more detail hereinafter, the resin-inpregnated foam materials of the present invention may also be used as walking heels or laminates between casts and walking heels, as supports for orthotic devices such as arch supports for foot orthotics, and as protective coverings for animal hoofs. In this regard, the resin-impregnated foam materials conform to virtually any surface, regardless of how irregular it may be, while still providing a relatively even walking surface on the opposing side.

DETAILED DESCRIPTION OF THE PREFERRED EMBODIMENTS

A. Orthopedic Splints

The subject matter of the present application is a continuation-in-part of the subject matter of copending application Ser. No. 015,972, filed Feb. 18, 1987 for "Orthopedic Splinting Articles and Methods," which is a continuation-in-part of application Ser. No. 784,345, filed Oct. 4, 1985 for "Orthopedic Casting Article and Method" (now U.S. Pat. No. 4,683,877). U.S. Pat. No. 4,683,877 discloses an orthopedic casting article and method for forming an orthopedic cast around an animal body utilizing a unitary blank which comprises a pliant, extensible layer of a foam member, an extensible fabric bonded to the foam member, and a curable resin impregnatably associated with the foam member.

The subject matter of application Ser. No. 015,972 is directed to an orthopedic splinting article and method for forming an orthopedic splint part way around an animal body part, and utilizes some of the principles disclosed in U.S. Pat. No. 4,683,877. For example, the orthopedic splinting article of application Ser. No. 015,972 utilizes a sheet of foam impregnated with a curable resin; however, no extensible fabric is bonded to the foam sheet prior to its application as a splint. Other features and parameters have been discovered and carefully tailored such that a resin impregnated foam sheet itself may be used effectively as an orthopedic splint.

For example, as disclosed in application Ser. No. 015,972, it has been discovered that a relatively soft, low density, highly flexible foam sheet can be impregnated with sufficient resin to render the impregnated foam rigid enough to function as an orthopedic splint, yet maintain safe exotherm during cure and sufficient water vapor porosity after cure so that skin maceration is substantially avoided. Reference will now be made to the drawings wherein like parts are designated with like numerals throughout.

Figure 1:
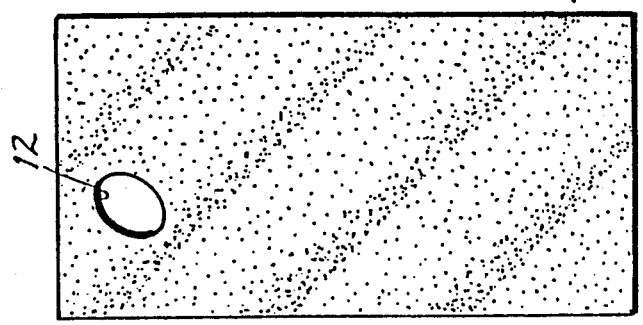
FIG. 1 is a plan view of a preferred forearm embodiment of the orthopedic splinting article of the present invention prior to application.
Figure 2A:
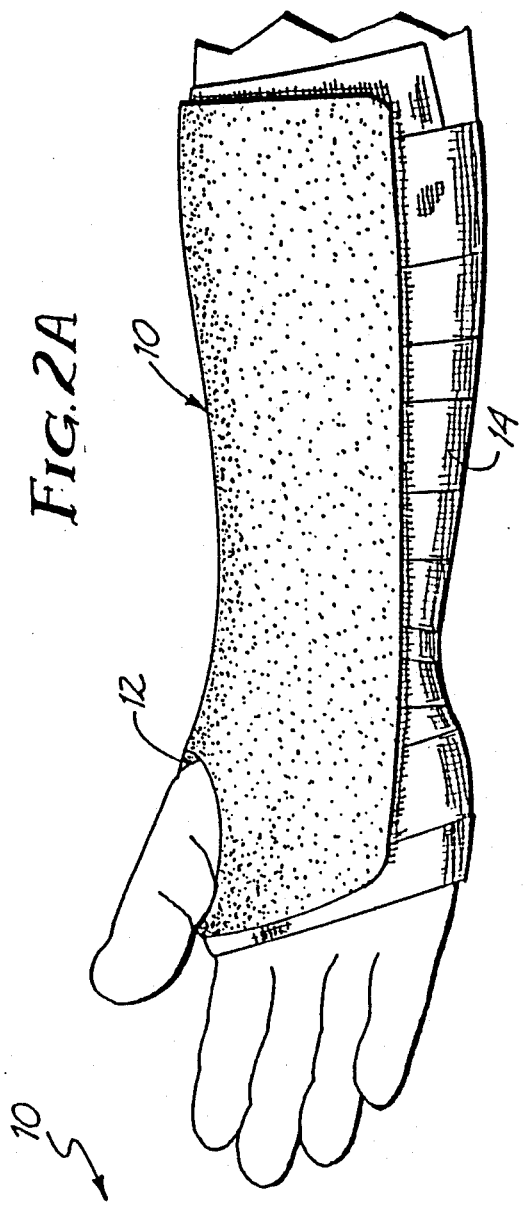
FIG. 2A is a perspective view of one side of the orthopedic splinting article of FIG. 1 which has been trimmed to fit an formed into a forearm splint.
Figure 2B:
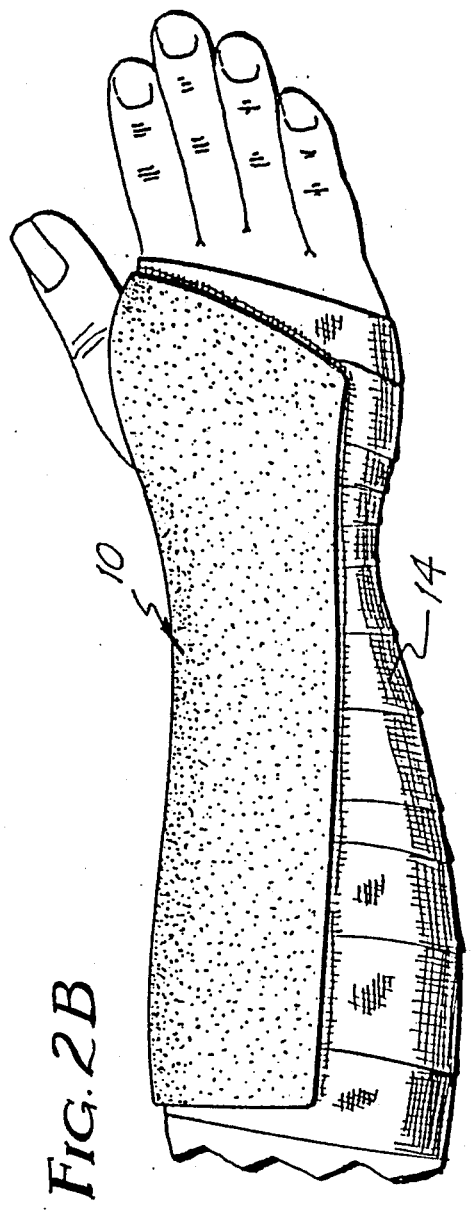
FIG. 2B is a perspective view of the opposite side of the orthopedic splinting article shown in FIG. 2A.

Referring now to FIG. 1, there is shown in plan view a preferred forearm orthopedic splinting article 10 of the present invention in the form of a unitary blank. The article or blank 10 is generally comprised of a pliant, extensive layer or sheet of a foam member, and preferably has a thumbhole 12 formed therein to facilitate application of the article 10 around a wearer's forearm as shown in FIG. 2. Article 10 of FIG. 1 is initially configured as a rectangle, and is then trimmed to custom fit the patient as shown in FIGS. 2A and 2B. In this regard, the physical characteristics of the foam material allow for easy trimming without leaving rough edges.

The foam sheet of article 10 is open-celled, and a curable resin is impregnatably associated with the foam sheet. As used herein, the term "open-celled" refers to a foraminous structure having interconnecting or communicating orifices or cavities therein caused by a sufficient number of the wall membranes of the foam cells having been removed to allow impregnation of the foam sheet 10 with an effective amount of the resin so that an efficacious splint can be formed. Further, as used herein, the term "impregnated" refers to the condition in which the resin is thoroughly intermingled with and in surrounding relation to the wall membranes of the cells and the interconnected cell frame members of the foam sheet 10.

The foam sheet of article 10 can comprise any one of a number of extensible foams which are open-celled, such as polyether or polyester based polyurethane foams. Importantly, the porosity of the foam sheet 10 must be such that it can be resin loaded sufficiently to provide a satisfactory orthopedic splint. In this regard, the open-celled foam sheet preferably has from about 30 to about 120 pores per inch. As used herein, the term "pores per inch" refers to the average number of pores located along a linear inch of the foam sheet. The number of pores per linear inch may be determined, for example, by measuring the foam's resistance to air flow or a pressure differential and using such information to calculate the approximate number of pores in the foam.

When the pores per inch value is decreased below 30, the foams become too course or rough, and typically do not hold enough resin to provide the necessary strength for the resulting orthopedic splint. Foam sheets having over about 100 pores per inch are not known to be presently commercially available. It will be understood, however, that the upper limit for the pores per inch parameter is limited solely by the ability to resin load the foam sheet to the extent needed to provide sufficient strength for an orthopedic splint, while still maintaining adequate porosity. Since foam sheets having over 100 pores per inch are not presently available, it is difficult to currently predict the performance of foams having substantially greater than 100 pores per inch as to their resin loading characteristics and porosity. Thus, in the most presently preferred embodiment of the present invention, the open-celled foam sheet used to form article 10 has from about 45 to about 100 pores per inch.

Foam sheet thicknesses of between about 5/16 of an inch to about ¾ of an inch are presently preferred, with a foam sheet thickness of about ½ inch being most presently preferred. Foam sheets much less than about 5/16 of an inch in thickness are generally too thin to yield a splinting article of sufficient strength at the maximum possible resin loading. Foam sheet thicknesses much greater than about ¾ of an inch tend to be too cumbersome and bulky for the patient and are aesthetically unpleasing. Furthermore, such thicker foam sheets may undesirably increase the exotherm felt by the patient during resin cure due to the increased insulative value of the thicker foam.

Figure 3:
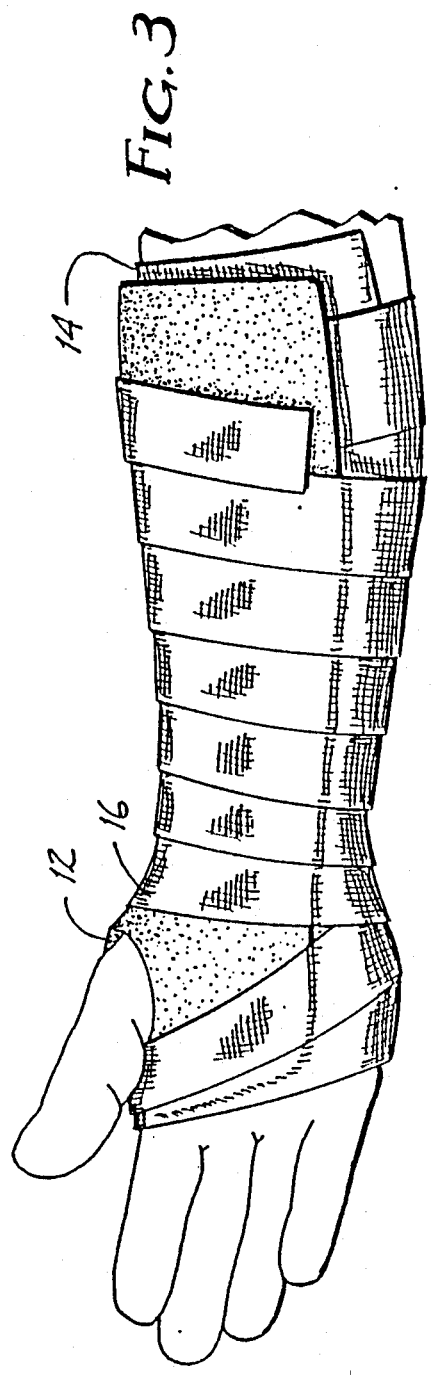
FIG. 3 is a perspective view of the embodiment of FIG. 2A additionally showing a stretch bandage which may be optionally wrapped around the splinting article in order to provide better conformability and attachment of the splinting article to the forearm.

For the forearm splint embodiment of FIGS. 1-3, a foam sheet approximately 7 inches wide, 12 inches long, and ½ inch thick is presently preferred. For the lower leg embodiment of FIGS. 4-5, a foam sheet approximately 10 inches wide, 38 inches long, and about ½ inch thick is presently preferred. However, it will be appreciated that the exact dimensions employed may vary according to the respective limb sizes of the individual to be treated.

The foam sheet utilized in article 10 preferably has a density in the range of about 1 to about 4.5 pounds per cubic foot, and most preferably, between about 1 and about 3 pounds per cubic foot. Foam sheets possessing densities lower than about 1 pound per cubic foot are not known to be presently commercially available. Foam sheets having densities higher than about 4.5 pounds per cubic foot tend to preclude the resin loading which is necessary to achieve proper splint strength.

One presently preferred material for the foam sheet of the present invention is a polyether based polyurethane foam sheet that is ½ inch thick and is presently available from Illbruck U.S.A., Minneapolis, Minn., as type E-150. It has been found that this foam material, when impregnated with a resin in accordance with the present invention, will provide a splint of sufficient strength and air permeability to be efficacious.

The presently most preferred resins for impregnating the foam sheet materials of the present invention are water curable, isocyanate functional, polyurethane prepolymers prepared by the reaction of a polyol with an excess of a polyisocyanate. The presently preferable polyurethane prepolymer resins have a relatively high viscosity. In this regard, after choosing an appropriate polyol and polyisocyanate to form the polyurethane prepolymer resin, the resultant prepolymer has a viscosity of at least about 75,000 centipoise or greater, and the presently most preferable embodiments of the present invention exhibit a viscosity of about 100,000 centipoise or greater.

It will be understood that the above viscosity values and all others set forth herein are values taken at room temperature (about 23° C.) and after a period of 24 hours following reaction of the polyol with the polyisocyanate. Further, all viscosity values set forth herein were measured under low humidity conditions using a Model RVT viscometer obtained from Brookfield Engineering Lab., Stoughton, Mass. 02072 equipped with spindle #6 (or spindle #7 in the case of viscosities greater than 100,000 centipoise) set at a rotational rate of 10 revolutions per minute (10 rpm). Thus, the viscosity values and ranges set forth herein necessarily relate to the viscosities which would be measured using such an apparatus and conditions; other apparatus and conditions may well provide other viscosity values.

The most important factors in the choice of an appropriate polyol and an appropriate polyisocyanate to form the polyurethane prepolymer resin are the NCO:OH ratio, that is, the number of isocyanate (NCO) groups in the polyisocyanate as compared to the number of hydroxyl (OH) groups in the polyol, and the NCO equivalent weight of the prepolymer. When these two parameters are controlled as taught herein, a splint can be formed having: (1) sufficient rigidity to immobilize a body member such that undesired movement, which would disturb or compromise the immobilized area, is substantially prevented, and (2) low enough exotherm to permit application to the body member without undesirably high levels of heat being liberated. In fact, in the presently preferred embodiments of the present invention, the exotherms are such that temperatures of 48° C. or less are felt by the patient, with temperatures of about 40° C. or less being felt by the patient in the most presently preferred embodiments.

In accordance with the foregoing, the NCO:OH ratio of the reactants must be within the range of about 2:1 to about 3.5:1, and preferably within the range of about 2.5:1 to about 3.0:1. It has been found that NCO:OH ratios lower than about 2:1 do not provide enough excess isocyanate groups to achieve adequate crosslinking of the resin during cure, while NCO:OH ratios greater than about 3.5:1 tend to produce undesirable exotherms (when industry standard isocyanate equivalent weights are used) which could potentially burn the patient.

Further in this regard, the isocyanate equivalent weight in the resultant prepolymer is preferably relatively large. The isocyanate equivalent weight is defined as the grams of prepolymer per NCO group. For purposes of the present invention, it has been found that the isocyanate equivalent weight should be within the range of about 350 grams to about 1000 grams of prepolymer per NCO group, and preferably within the range of about 370 grams to about 600 grams of prepolymer per NCO group. The average hydroxyl equivalent weight of the polyol before formation of the prepolymer, although less important, is generally about 200 grams to about 400 grams of polyol per OH group, and is about 220 grams of polyol per OH group in one very specific and presently preferred embodiment of the present invention.

Surprisingly, by using the relatively low NCO:OH ratios, relatively high isocyanate equivalent weights, and relatively high viscosity polyurethane prepolymers discussed herein, a low enough exothermic reaction can be achieved during cure to avoid burning the patient, even at high prepolymer resin content in the splint. At the same time, the rapid cure times and final rigidity needed for immobilization of the injured body member are also achieved.

The primary reason that such high viscosity polyurethane prepolymers (where the most preferable prepolymers have a viscosity of 100,000 centipoise or greater) may be employed in the present invention is that the polyol and polyisocyanate are preferably reacted in situ in the foam sheet, well before the final viscosity of 100,000 centipoise or greater is reached in the prepolymer product. In order to accomplish this, the polyol and polyisocyanate are mixed together, and the mixture is immediately squeezed or otherwise manipulated into the foam sheet so that the substantial portion of the polyol/polyisocyanate reaction takes place within the foam sheet itself. Alternatively, the polyol and polyisocyante could be independently squeezed into the foam sheet and mixed therein so as to react only upon their contact within the foam. Such procedures avoid the necessity of solvent coating the extremely viscous polyurethane prepolymer onto the foam sheet and the attendant disadvantage of having to subsequently remove the solvent, and the resultant resin impregnated foam sheet has relatively low exotherm and sufficient strength upon curing.

Although the in situ reaction technique outlined above is presently most preferred, there are other techniques, including additional solventless techniques, which could be used, if desired, to impregnate the prepolymer resin into the foam sheet. For example, it is also possible to first react the polyisocyanate and polyol to form the polyurethane prepolymer resin, heat the prepolymer resin to a temperature sufficient to significantly reduce its viscosity (for example, 60° C. or higher), immerse the foam sheet into the heated prepolymer resin, and squeeze the foam while thus immersed to impregnate the foam with the prepolymer resin. However, it should again be emphasized that the presently most preferable technique for impregnating the foam with the resin is by reacting the polyisocyanate and polyol in situ within the foam.

Surprisingly, the polyurethane prepolymer resin can be loaded into the foam sheets of the present invention so as to comprise from about 70% to about 95% by weight of the total article. Such a high degree of resin loading imparts to the cured article the necessary strength to function as an orthopedic splint. Also surprisingly, after loading such large percentages of resin into the foam, the resultant article has quite good water vapor permeability and porosity, thereby substantially avoiding skin maceration.

Examples of isocyanates used to form polyisocyanates which are suitable for purposes of the present invention are disclosed in U.S. Pat. Nos. 4,376,438, 4,433,680, and 4,502,479. Those isocyanates which are presently preferred include 2,4'-diphenylmethane diisocyanate, 4,4'-diphenylmethane diisocyanate, mixtures of these isomers together with possible small quantities of 2,2'-diphenylmethane diisocyanate (typically contained in commercially available diphenylmethane diisocyanates), and aromatic polyisocyanates and their mixtures such as are derived from phosgenation of the condensation product of aniline and formaldehyde. It is presently preferred to use an isocyanate which has low volatility such as diphenylmethane diisocyanate rather than a more volatile material such as toluene diisocyanate. Commercially available isocyanate starting materials include Isonate ® 143L available from Dow Chemical, Midland, Mich., which is a mixture of isocyanate compounds containing about 73% by weight of diphenylmethane diisocyanate, and Mondur ® MRS-10 available from Mobay Chemical Corp., New Martinsville, W.Va.

Examples of polyols which are suitable for purposes of the present invention include polyoxypropylene polyols, castor oil type triols, and polyester polyols. Specific polyols which are useful include polypropylene glycols such as PPG 425 and PPG 725 available from Union Carbide, Danbury, Conn., polypropylene triols such as LHT 240 available from Union Carbide, and castor oil polyols.

However, it will be understood that, as used herein, the term "polyol" also includes virtually any functional compound having active hydrogen in accordance with the well-known Zerevitinov test, as described, for example, in *Chemistry of Organic Compounds* by Carl R. Noller, Chapter 6, pp. 121-122 (1957). Thus, for example, thiols and polyamines could also be used as "polyols" in the present invention, and the term "polyols" will be considered to include such other active hydrogen compounds. In such instances, the NCO:active hydrogen ratio of the polyisocyanate to the active hydrogen compound used to form the polythiocarbamate, polyurea, or other polymer, should fall within the same ranges as disclosed herein for the NCO:OH ratios.

An especially preferred resin for use in the splint articles of the present invention includes the Mondur ® MRS-10 isocyanate available from Mobay Chemical, and a castor oil polyol available from Caschem, Bayonne, N.J. Another preferred resin may be formed by reacting Isonate ® 143L and the polypropylene oxide polyol available from Union Carbide as Niax ® polyol PPG 425. To prolong the shelf life of material, it is preferred to include about 0.02 to about 0.1 percent by weight of benzoyl chloride or other suitable stabilizer (e.g., an antioxidant such as butylated hydroxytoluene at a level of about 0.05 to about 0.5 weight percent).

Foaming of the resin which would reduce the porosity of the cured device and its overall strength should be minimized. Foaming occurs because carbon dioxide is released when water reacts with isocyanate groups. The most satisfactory method of minimizing foaming involves the addition of a foam suppressor such as silicone Antifoam A (Dow Corning, Midland, Mich.), DB-100 silicone fluid (Dow Corning), or silicone surfactants L550 or L5303 (Union Carbide) to the resin. It is presently preferred to use a silicone liquid such as Dow Corning DB-100 at a concentration of about 0.1 to about 1.0 percent by weight.

It is possible to make the curable resin of the present invention less tacky in accordance with the invention described in commonly assigned U.S. Pat. No. 4,667,661 for "Curable Resin Coated Sheet Having Reduced Tack," which patent is incorporated herein by reference. Reduced tackiness may be achieved by a number of means as described in U.S. Pat. No. 4,667,661, the result being that the kinetic coefficient of friction of the surface of the splinting article is less than about 1.2, when measured according to the procedure of ASTM-D-1894 with one slight modification. (This modification is that, instead of covering the test sled with a layer of the material to be tested as called for in the procedure of ASTM-D-1894, the test sled was instead covered only with a layer of aluminum foil.) One technique for achieving such tack reduction is to lightly spray the surfaces of the resin-impregnated article 10 with a mixture of a polydimethylsiloxane, having a viscosity of at least about 100 centistokes, and polyethylene oxide long chain aliphatic hydrocarbon waxes. Alternatively, a small amount of a polyethylene oxide-polypropylene oxide block copolymer may be added to the polyol during prepolymer preparation, after which the polydimethylsiloxane may be sprayed onto the surface of the article 10 as before. The polydimethylsiloxane reduces resin tackiness prior to contact with water. The hydrophilic polyethylene oxide materials provide additional tack reduction upon contact with water.

Reduced resin tack facilitates application of the splinting article 10 to the patient's limb. However, the orthopedic splinting articles of the present invention can be successfully applied without reducing tack. In this regard, it has been surprisingly found that the polyurethane resin impregnated foam articles of the present invention already experience much less tack than would normally be expected. It is believed that one reason for this may be that the majority of the resin is contained away from the surfaces of the foam sheet, thereby resulting in less tack at the surfaces. Hence, the polyurethane resin impregnated foam articles of the present invention already have reduced tack, and a tack reducing agent need not necessarily be employed.

The polyurethane prepolymer resin of the present invention also preferably contains a catalyst to control the set time and cure time of the resin. To produce suitable orthopedic splint devices in accordance with the present invention, a set time of about 3-18 minutes following activation of the polyurethane resin by dipping in water is preferred, with the most preferable set time being about 4-10 minutes. Suitable catalysts for moisture curing polyurethane prepolymer resin systems are well known. For example, tertiary amine catalysts such as 2,2'-dimorpholinodiethyl ether (DMDEE) described in U.S. Pat. No. 4,433,580 and 4-[2-[1-methyl-2-(4-morpholinyl)ethoxy]ethyl]morpholine (MEMPE) described in assigned U.S. Pat. No. 4,705,840, in amounts ranging from about 0.5% to about 5% by weight of the resin system, may be used for this purpose.

The resin impregnated foam sheets of the present invention are preferably prepared in a relatively low humidity chamber and sealed within a water vapor impermeable package. This package is opened just prior to application of the orthopedic article. Using such a system, the resin impregnated foam sheets of the present invention are relatively storage stable.

Optional elements of the orthopedic splinting articles of the present invention and one presently preferred method by which orthopedic splints can be formed in accordance with the present invention will now be described with reference to FIGS. 1, 2A, 2B, and 3. Referring first to FIG. 1, the orthopedic splinting article 10 is sized according to the forearm of the patient, and may be trimmed prior to application in order to provide a more exact fit. The thumbhole 12 may be formed by either punching or cutting out a corresponding portion of article 10.

Before actually applying article 10 to the forearm, a flexible stockinet or cast padding 14 is preferably placed around the patient's forearm so as to prevent undesirable adhesion or contact between the splint and forearm of the patient. For example, a tubular padding material, such as one side lofted tubular fabric made on an athletic sock machine available from Broadway Knitting Mills, 2152 Sacramento Street, Los Angeles, Calif. 90021, may be used for this purpose.

The splint of FIGS. 2A, 2B, and 3 is formed by first activating the resin of article 10 of FIG. 1 with water. Next, the left or right hand thumb of the patient is passed through aperture 12, and the long edge of the rectangular article is longitudinally aligned with the patient's forearm. The article is then circumferentially molded or positioned around the forearm to the position shown in FIGS. 2A and 2B. In this regard, the resin impregnated foam has excellent compression moldability or conformability to provide a good fit around the patient's forearm.

The article 10 is sufficiently dimensioned in its longest direction to extend the length of the forearm to be immobilized by the splint. The article 10 is dimensioned in the other direction so as to accommodate swelling of the forearm. This is preferably done by configuring article 10 so that it extends partially, but not completely, around the circumference of the forearm. In this regard, in order to accommodate the swelling of the forearm, the orthopedic splint 10 preferably extends around about 40% to about 90% of the circumference of the forearm, and most preferably around about 60% to about 75% of the circumference of the forearm. Such partial enclosure allows for swelling of the injured forearm, yet provides adequate immobilization thereof to promote healing.

However, it will be appreciated that the splinting article could also be configured in the circumferential direction so as to completely surround the forearm if desired. In order to accommodate swelling in such an instance, it is important that there remain a longitudinal break in the splinting article. Thus, although not the presently preferred embodiments, the splinting article could be merely wrapped around the forearm until the longest edges come into close proximity or even meet (without sealing the edges), or alternatively, so that the longest edges actually overlap slightly, but again without sealing the edges together so that the splint could still expand to accommodate swelling. Means to prevent sealing of the edges include the use of a nonadhering layer inserted between overlapping edges.

It should be noted that the accommodation of swelling involves at least two considerations. First, the orthopedic splint must provide for the accommodation of the swelling tissue itself. Second, the orthopedic splint should also be capable of manual expansion if necessary to accommodate even further swelling of the tissue. Thus, although the splint must be sufficiently rigid to immobilize the injured limb, it is desirable that the splint not be so rigid that some manual expansion is not possible when needed. The orthopedic splints of the present invention exhibit such properties.

The orthopedic splinting article 10 is preferably held in place while the resin is curing by the aid of securing means. For example, wrapping means such as a stretch bandage 16 shown in FIG. 3 may be used to secure article 10 around the forearm during curing so that the resultant orthopedic splint will conform well to the forearm. Although a right arm is shown in FIGS. 2A, 2B, and 3, it will be understood that the splinting article 10 may be applied equally well to a left arm.

After application, article 10 can be easily adjusted or repositioned during curing (but prior to setting of the resin) without substantial wrinkling. Furthermore, after curing and after the splint has served its intended purpose, the splint can be removed from the patient's forearm by unwrapping the stretch bandage and then prying open the splint. The general U-shape of forearm splint 10 shown in FIGS. 2A and 2B has been found to exhibit excellent strength and resistance to breakage.

In summary, the orthopedic splinting article 10 of the present invention can be applied to a forearm by: (1) exposing the article to water to initiate hardening of the resin, (2) manually squeezing out excess water, (3) properly positioning the orthopedic splinting article over a stockinet or cast pad applied to the forearm, (4) trimming the orthopedic splint to the desired shape, and (5) holding the splint in place as the resin cures, e.g., by wrapping a stretch bandage or other securing means around the splint article and forearm to secure the splint in place.

Figure 4:
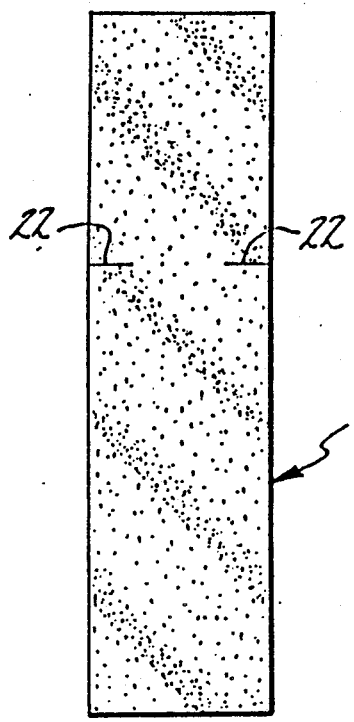
FIG. 4 is a plan view of a preferred lower leg embodiment of the orthopedic splinting article of the present invention prior to application.
Figure 5:
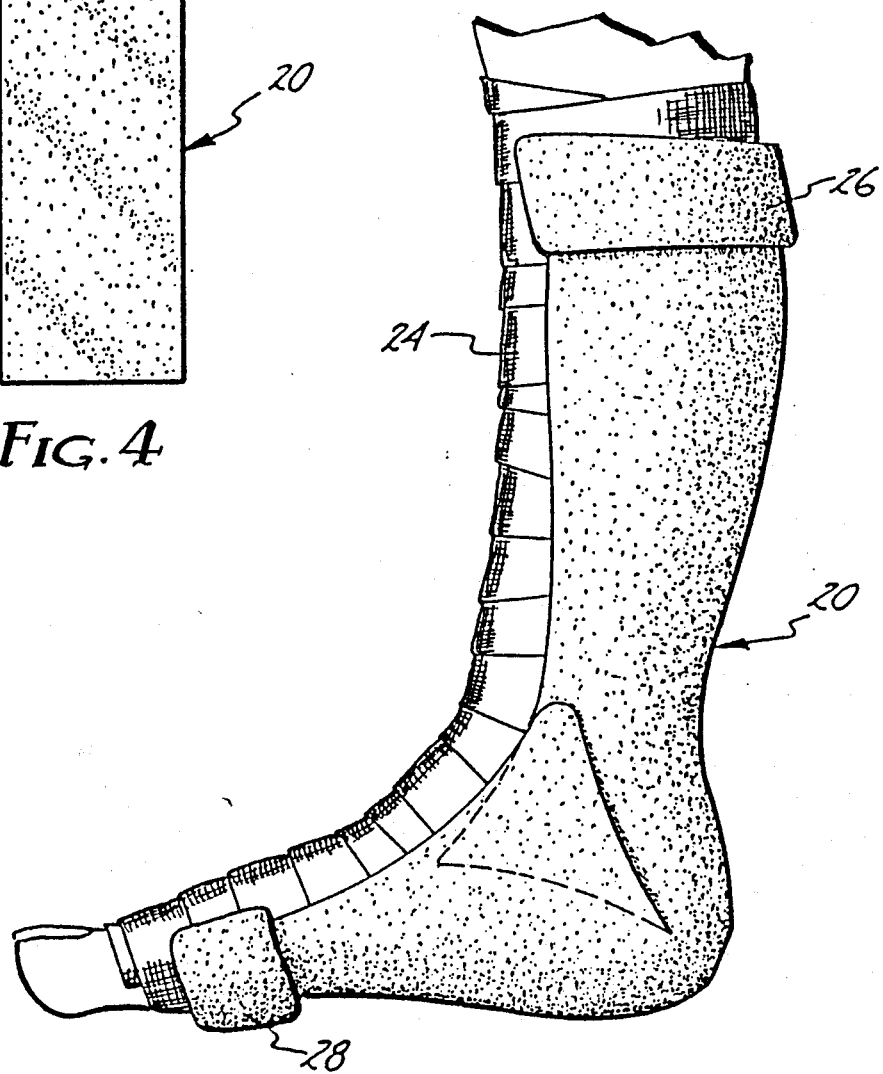
FIG. 5 is a perspective view of the orthopedic splinting article of FIG. 4 formed into a lower leg splint.

The lower leg embodiment of the splinting article of the present invention will now be explained with reference to FIGS. 4 and 5. The lower leg splinting article 20 of FIGS. 4 and 5 is generally comprised of a unitary blank which has the same composition and characteristics of blank 10 used in the forearm application. Hence, the disclosure herein relating to forearm article 10 and the method of FIGS. 1-3 relates also to lower leg article 20 and the method of FIGS. 4-5, with the basic exception that lower leg article 20 is dimensioned somewhat larger in order to partially enclose the lower leg of the patient. Preferably, a cast padding 24 is also used between lower leg splint 20 and the patient's lower leg.

To facilitate application of splint 20, two slits 22 are preferably formed in splint 20 which, as shown best in FIG. 5, allow for some overlapping of the material to form an ankle and heel pocket in the splint around the patient's ankle and heel, and thereby avoid bulky material folds which would otherwise be experienced without such slits. These slits 22 are preferably formed by the physician applying the lower leg splint so that the splint can be precisely tailored particular patient's leg size. Furthermore, it may be desirable to fold the foam material over at the patient's calf to form a fold 26 or at the patient's toes to form a fold 28 so as to customize lower leg splint 20 to the appropriate proportions of the patient's lower leg. Additionally, fold 28 provides additional strength at the extremities of the splint 20 where weight bearing characteristics become more important. Although not shown in FIG. 5, a stretch bandage or other securing means should also be applied around lower leg splint 20 so as to secure the splint in place and to provide better conformability to the lower leg during curing.

It will be understood that various modifications and changes may be made by those skilled in the art to accommodate different situations. For example, a simple cylindrical splint may be formed in accordance with the present invention so as to immobilize an upper or lower arm, an upper or lower leg, or even a knee. By a cylindrical splint article, it is meant that the article does not necessarily include a thumbhole or heel pocket, etc.

The present invention will be further understood in view of the following examples which are merely illustrative and are not to be considered as comprehensive or limiting in any way.

EXAMPLE 1

In this example, a forearm splint within the scope of the present invention was prepared. First, a polyether based polyurethane foam was procured from Illbruck U.S.A. as Type E-150, and cut to a thickness of about $\frac{1}{2}$ inch. This foam material has a density of about $1.5 \pm 0.1$ lbs/ft$^3$, and a pore size of about 60 pores per lineal inch. A 7 inch by 12 inch sheet of this foam material was cut, and a thumb hole was placed in the material in the approximate position shown in FIG. 1. The weight of the foam sheet was determined to be about 22 grams, and this figure was used to determine the correct amount in grams of the resin to be used in order to achieve a resin loading of about 85% by weight of the final resin impregnated foam sheet.

A polyurethane prepolymer resin having an NCO-:OH ratio of about 3.0:1 was prepared as follows. In an atmosphere maintained at about 4% relative humidity, a vessel was charged with about 396 grams of Mondur ® MRS-10 obtained from Mobay Chemical. (This isocyanate compound has an NCO equivalent weight of about 132 grams of isocyanate per NCO group.) A second vessel was charged with about 342 grams of castor oil as the polyol, which was obtained from Caschem. (The castor oil had an OH equivalent weight of about 342 grams of polyol per OH group.) To the castor oil in the second vessel was added about 0.74 grams of benzoyl chloride, and about 9 grams of 4-[2-[1-methyl-2-(4-morpholinyl)ethoxy]ethyl]morpholine (MEMPE) prepared as described in U.S. Pat. No. 4,705,840. The mixture in the second vessel was then added to the isocyanate compound contained in the first vessel, and the components were blended together. (This prepolymer mixture had an NCO equivalent weight of about 374 grams of prepolymer mixture per NCO group.) Immediately after blending these components together, the blended resin mixture was impregnated into the foam sheet in an amount such that the resin represented about 85% by weight of the final product. Such impregnation of the resin into the foam sheet was achieved in a moisture-free chamber by spreading the resin over all surfaces of the foam sheet and then manually kneading the resin into the foam material. The viscosity of the polyurethane resin, after reaction of the components, was determined to be about 200,000 centipoise. The splint article thus prepared was then sealed in an air-tight pouch to protect the article from exposure to moisture.

Later, the forearm splint article prepared in this Example 1 was applied to a human forearm using the following procedure. First, a conventional cast padding was wrapped around the forearm. Next, the splint article was removed from the air-tight pouch and trimmed to more precisely fit the forearm. The article was then submerged in water and squeezed several times in order to ensure proper activation of the resin, lifted out of the water, and excess water was squeezed out. The article was then placed around the forearm to provide a good fit. In order to hold the splint in place during curing and provide better conformability and moldability to the forearm, a stretch bandage was wrapped around the splint article immediately after placing the article around the forearm. The splint article extended about 75% around the forearm and the exotherm was such that a temperature (measured by thermocouples inserted next to the skin) of about 40° C. was observed during curing. After about 5 minutes from the initial water activation of the resin, the splint was sufficiently rigid to support the forearm. There was no apparent moisture or dampness retained against the surface of the skin under the cured splint.

EXAMPLE 2

In this example, a forearm splint within the scope of the present invention was prepared and applied to a human forearm in accordance with the procedure of Example 1 with the following exceptions. In this Example 2, a polyurethane prepolymer resin having an NCO-:OH ratio of about 2.5:1 was prepared by charging the first vessel with about 360 grams of Isonate ® 143L obtained from Upjohn. The second vessel was charged with about 216 grams of Niax ® polyol PPG 425 obtained from Union Carbide, about 0.58 grams of benzoyl chloride, and about 7 grams of MEMPE catalyst. Thus, in this example, the prepolymer resin represented about 80% by weight of the final product, and the prepolymer resin had an NCO equivalent weight of about 388 grams of prepolymer resin per NCO group. The prepolymer resin, before moisture curing, had a measured viscosity in excess of 200,000 centipoise. The temperature which would be felt by the patient during curing was measured to be about 39° C. The forearm splint formed in this example was found to be efficacious and was sufficiently set after about 5 minutes from the initial activation of the prepolymer resin.

EXAMPLE 3

In this example, a lower leg splint within the scope of the present invention was prepared and applied to a lower leg in accordance with the procedure of Example 1 with the following exceptions. For this lower leg application, a foam sheet was cut from the $\frac{1}{2}$ inch foam material having dimensions of about 10 inches by about 38 inches. A slit about 3 inches long was cut into each 38 inch edge about 12 inches from the end of the foam sheet similarly to slits 22 shown in FIG. 4. The lower leg splint article prepared was then applied around a human lower leg and the material adjacent the slits was overlapped as shown in FIG. 5 so as to form an ankle/heel pocket. The curing time, exotherm observed, and other data observed were the same in this Example 3 as in Example 1 above.

EXAMPLES 4 AND 5

In these examples, orthopedic splinting materials within the scope of the present invention were prepared in order to show the relative rigidity of the materials. In Examples 4 and 5, the orthopedic splinting materials were not applied to any limb, but were rather tested for their elongation after curing. The materials of Examples 4 and 5 were prepared in accordance with the procedure of Example 1, with the following acceptions. In both Examples 4 and 5, a polyurethane prepolymer resin having an NCO:OH ratio of about 3 to 1 was prepared by charging the first vessel with about 432 grams of Isonate® 143L obtained from Upjohn. The second vessel was charged with about 216 grams of Niax® polyol PPG 425 obtained from Union Carbide, about 0.65 grams of benzoylchloride, and about 8 grams of MEMPE catalyst. Further, the foam materials used in Examples 4 and 5 were a 4"×8"×½" piece of P-100 foam (having 100 pores per inch) available from Illbruck U.S.A., Minneapolis, Minn., and a 4"×8"×½" piece of P-45NR foam (having 45 pores per inch) available from Illbruck U.S.A., respectively. In Example 4, enough of the prepolymer resin was impregnated into the P-100 foam such that the prepolymer resin represented about 80% by weight of the final product. In Example 5, enough prepolymer resin was impregnated into the P-45NR foam such that the prepolymer resin represented about 85% by weight of the final product. Each resin impregnated foam sheet was placed in a foil pouch and sealed.

Later, the resin impregnated foam sheets were removed from their respective foil pouches, dipped in water to activate the prepolymer resin, and allowed to cure for several days. During curing of the resin impregnated foam sheet of Example 4, the foam was compressed to about ½ of its normal thickness (i.e., compressed to about ¼") during cure so as to simulate the compression which would typically occur when wrapping the material around an injured body part.

After curing was complete, each of the cured sheets was cut into six strips which measured ½ inch wide and 4 inches long. Each of these strips was then tested for maximum elongation before breaking. For this purpose, each cured strip was mounted in pneumatic grips which were attached to a TTM Table Model Instron apparatus equipped with a 50 kilogram load cell. The test conditions were set as follows:

Chart=50 cm/min
Crosshead Rate=5.0 cm/min
Gauge Length=5.0 cm/min

Each of the sample strips was elongated until it broke. The ultimate elongation for each of the strips tested in Examples 4 and 5 was measured to be less than 1.5% of the original strip length. Hence, Examples 4 and 5 evidence the relative rigidity of the resin impregnated foam sheets of the present invention after curing has been completed.

B. Walking Heels or Laminates Between Casts and Walking Heels

The resin-impregnated materials of the present invention, due to their conformity, are very useful in providing a material which conforms to the bottom of an irregularly shaped surface, but which at the same time provides an even, smooth, weight bearing surface, such as is needed in the case of walking casts and orthotic devices. In this regard, it is common in the prior art to attach a preformed rubber sole or heel to the bottom of a foot or leg cast in order to provide mobility and traction for the wearer. However, prior art attachment methods typically involve wrapping the preformed heel or sole with additional casting material to attach it to the cast; this adds significant extra weight to the assembly. Furthermore, the bottom surface of the cast is often irregular, and this is further complicated in the instance where the cast has been formed around a deformed foot. In such instances, it has been extremely difficult in the prior art to provide proper orientation between the walking heel and the floor or surface on which the patient must walk.

Prior art attempts to apply a walking heel to the cast of a patient with a deformed foot include the use of dams to properly orient a piece of plywood board with the bottom of the cast, and then resin is injected into the space defined by the dams, cast bottom, and plywood. The walking heel is then anchored to the plywood after the resin has cured. Not only is such a curable resin system cumbersome, but the resulting product bears significantly extra weight. By using the relatively lightweight resin-impregnated foam materials of the present invention, a material is provided that can readily serve either as the laminate between the bottom of the cast and the walking heel or as the walking heel itself.

Figure 6A:
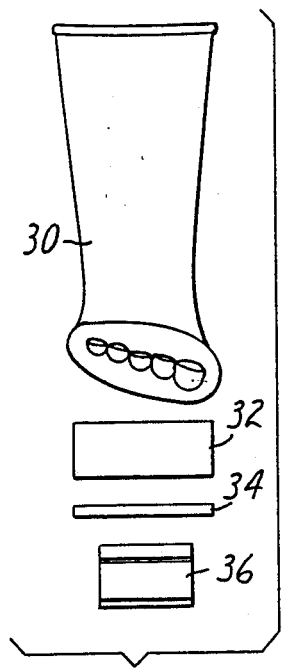
FIG. 6A is an exploded front view of one embodiment of the present invention when used as a laminate between a foot cast and a walking heel.
Figure 6B:
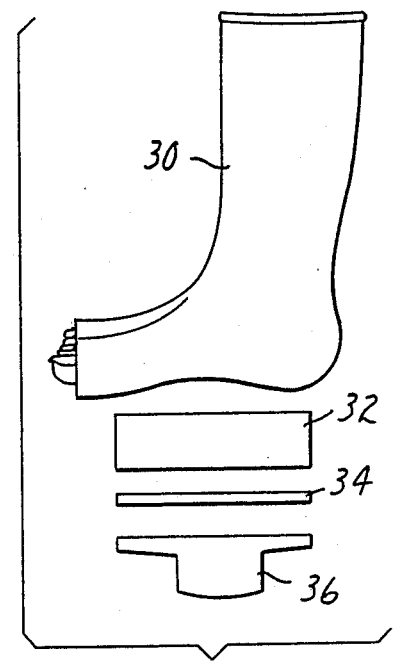
FIG. 6B is a side view of the embodiment of FIG. 6A.
Figure 6C:
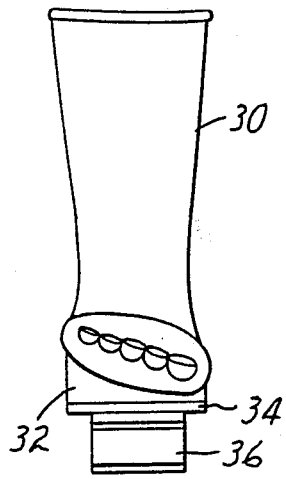
FIG. 6C is an assembled view of the components of FIG. 6A.
Figure 6D:
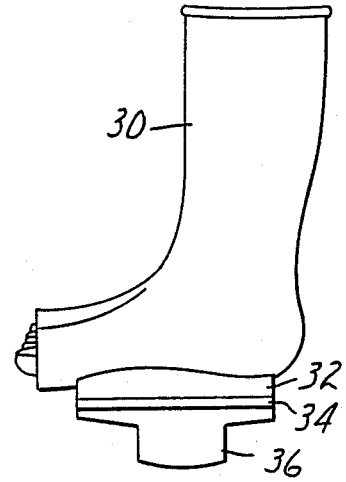
FIG. 6D is a side view of the embodiment of FIG. 6C.

Referring now to FIGS. 6A through 6D, the utilization of the resin-impregnated foam material as a laminate between the cast covering a deformed foot and a walking heel to be applied thereto is illustrated. First, a resin-impregnated foam block 32 made in accordance with the present invention (which has been activated by dipping in water) is applied to the irregular surface of cast 30 which has been formed around a deformed foot. As seen in FIGS. 6C and 6D, the conformability of resin-impregnated foam material 32 allows the material to follow the irregular contours of cast 30 and yet provide an even surface for applying a plywood support plate 34 thereto. In one presently preferred embodiment, plywood support plate 34 is brought to bear against the bottom surface of resin-impregnated foam block 32 in an orientation parallel with the floor so as to cause material 32 to have the proper bottom orientation and compress to cast 30 as needed to conform with the irregular surface thereof. Because of the adhesive nature of resin-impregnated foam block 32, sufficient adherence between block 32 and cast 30 as well as between block 32 and plywood plate 34 is provided without the use of additional securing means. Preformed walking heel 36, preferably made up rubber or other suitable material, is then anchored to plywood plate, for example, by the use of one or more screws (not shown).

The finished assembly, shown in FIGS. 6C and 6D, is relatively lightweight as compared with the prior art, due primarily to the lightweight of resin-impregnated foam material 32. Moreover, as seen in FIGS. 6C and 6D, foam material 32 conforms well to the bottom side of cast 30 while providing an even and properly oriented bottom surface for applying plywood plate 34 and walking heel 36 thereto. Further, the resin-impregnated foam material 32 actually adds strength to finished cast 30. Because the resin-impregnated foam material 32 compresses so as to conform to the bottom of cast 30, walking heel 36 can be attached so that it impacts the ground squarely without the use of shims or other techniques to properly orient the heel.

Figure 7A:
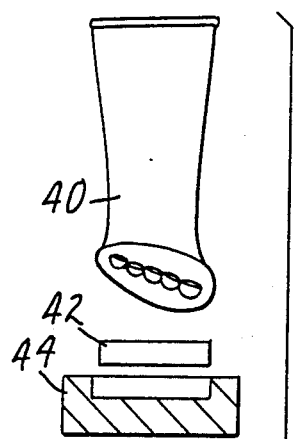
FIG. 7A is a front view illustrating one embodiment of the present invention showing how the resin-impregnated foam material may be applied as the walking heel itself.
Figure 7B:
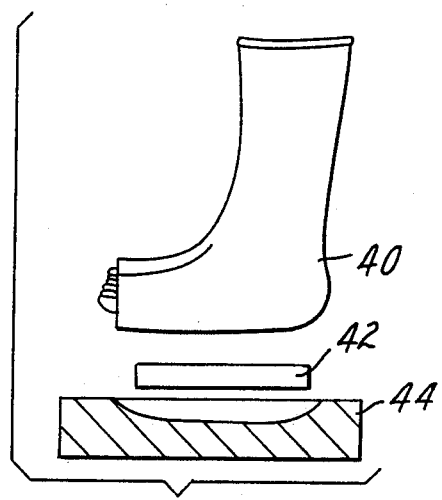
FIG. 7B is a side view of the embodiment of FIG. 7A.

FIGS. 7A through 7D illustrate how the resin-impregnated foam materials of the present invention may be used in and of themselves to form a walking heel for a foot or leg cast. As seen in FIGS. 7A and 7B, an activated resin-impregnated foam block 42 within the scope of the present invention is oriented between the cast 40 formed around a deformed foot of a patient and a form or mold 44 which is used to shape the bottom surface of foam block 42. Pressure is then applied by the patient in forcing cast 40 against resin-impregnated foam block 42 down into mold 44. The form is made of or coated with a material which will not stick to foam block 42 such that, after curing, mold 44 may be removed from block 42 providing the assembly shown in FIGS. 7C and 7D.

Figure 7C:
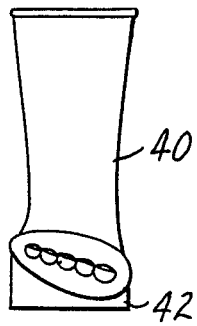
FIG. 7C illustrates a front view of the finished cast/walking heel product formed in FIG. 7A.
Figure 7D:
FIG. 7D is a side view of the finished cast/walking heel of FIG. 7C.
Figure 8A:
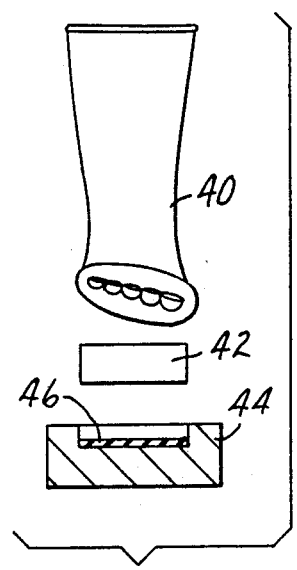
FIGS. 8A and 8B correspond to an embodiment similar to FIGS. 7A and 7B, with the exception that a rubber sheet is positioned to be applied to the walking heel so as to form a wear surface thereon.
Figure 8B:
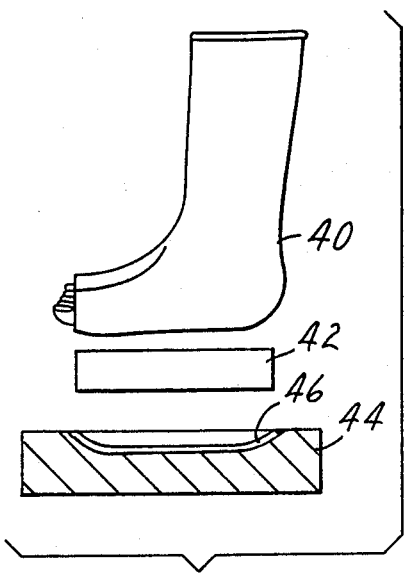
Figure 8C:
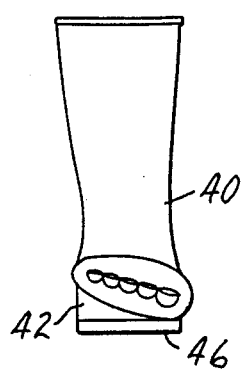
FIGS. 8C and 8D correspond to FIGS. 7C and 7D, with the addition of the rubber wear surface.
Figure 8D:
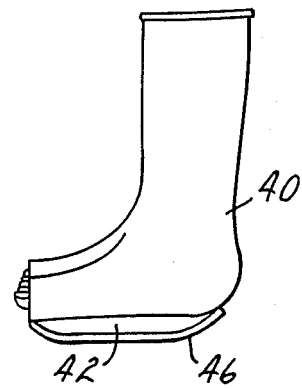

As seen in FIGS. 7C and 7D, resin-impregnated foam block 42 again conforms to the irregular surface of cast 40 and yet provides a properly aligned and curved walking heel 42 on the bottom surface thereof. Moreover, the resin-impregnated foam material 42 adds strength to cast 40 and effects relatively equal distribution of the patient's weight over the entire bottom of cast 40.

It will be understood that the walking heels of the present invention can be given a variety of desired configurations and are not limited to the shapes shown in FIGS. 7C and 7D. For example, in some instances, it may be desirable to provide a walking heel having a curved end at the toe or front portion of the cast and a square end at the heel or back portion of the cast (instead of the curved heel portion shown in FIG. 7D).

If desired, a rubber sheet 46 can be applied to walking heel 42 so as to provide a rubber wearing surface therefor; this embodiment is shown in FIGS. 8A through 8D. Hence, the only difference between the embodiment of FIGS. 8A through 8D and the embodiment of FIGS. 7A through 7D, is that a rubber sheet 46 is placed in mold 44 in the embodiment of FIGS. 8A through 8D. Hence, when cast 40 is pressed down against resin-impregnated foam block 42 and into mold 44, rubber sheet 46 becomes sandwiched between block 42 and mold 44 and is firmly attached thereto. The result is the assembly shown in FIGS. 8C and 8D wherein walking heel 42 has a rubber wear surface 46 attached thereto.

C. Supports for Orthotic Devices

The resin-impregnated foam materials of the present invention are also useful as supports for orthotic devices such as arch supports for foot orthotics, as shown in FIGS. 9A through 9D.

When a foot orthotic is formed, it is necessary to place some sort of support beneath the orthotic so that the orthotic will not flatten out when walked upon. The prior art has used hot melt adhesives as such supports. Unfortunately, this requires the use of molds or forms to inject the hot liquid adhesive. The resin-impregnated foam materials of the present invention, on the other hand, may be applied much more simply as a support for a foot orthotic.

Figure 9A:
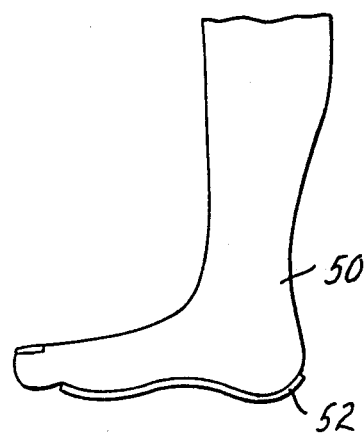
FIG. 9A illustrates the formation of a foot orthotic.

Referring now to FIG. 9A, a foot orthotic 52 is formed around the foot 50 of a patient using, for example, multiple layers of a resin-impregnated fiberglass orthopedic casting tape such as Scotchcast® 2 casting tape sold by 3M, St. Paul, Minn. Thus, orthotic 52 is a conventional foot orthotic as is already known in the art.

Foot orthotic 52 is first formed with the desired arch using a procedure such as the following. First, a relatively large piece (for example, 8 inches by 14 inches) of relatively soft foam is covered with a piece of plastic film. Several layers of orthopedic casting tape such as Scotchcast® 2 orthopedic casting tape are dipped in water so as to activate the material and are then placed on the plastic film. The foot of the patient, which has been covered with a stockinette, or plastic film, or other protective material, is pressed down into the orthopedic casting tape. The patient's foot remains in this position until the casting tape has cured. The orthotic so formed is then cut into a shape corresponding to the patient's foot.

Figure 9B:
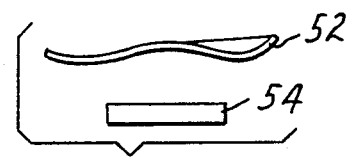
FIG. 9B shows the foot orthotic so formed in conjunction with a resin-impregnated foam material of the present invention.
Figure 9C:
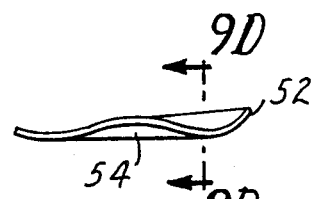
FIG. 9C illustrates how the resin-impregnated foam material of the present invention conforms to the bottom of the foot orthotic, and yet forms an even walking surface on the bottom side thereof.
Figure 9D:
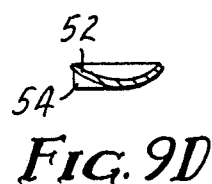
FIG. 9D is a back view of the orthotic/resin-impregnated material assembly of FIG. 9C.

Referring now to FIG. 9B, once orthotic 52 has been formed, an activated resin-impregnated foam block 54 within the scope of the present invention is oriented directly below the arch of foot orthotic 52. As seen in FIGS. 9C and 9D, the rigid foot orthotic shell is then pressed down on the activated resin-impregnated foam block 54. Again, the foam compresses to conform to the bottom contours of orthotic 52, while providing a flat support surface on the bottom of block 54.

Thus, the resin-impregnated materials of the present invention provide a pliant, extensible, and extremely conformable substrate which provides a transition layer from the various contours of orthotics to the flat walking surface typically encountered in normal ambulation.

It will be appreciated that the resin-impregnated foam materials of the present invention may be used to support other orthotics besides foot orthotics. Further, the materials of the present invention, when used to support foot orthotics, may be used to support other areas besides the arch. For example, a piece of resin-impregnated foam material within the scope of the present invention may also be used to support the heel of a foot orthotic (such as the foot orthotic shown in FIGS. 9C and 9D), thereby acting as a heel post (not shown in the Figures).

D. Protective Coverings for Animal Hoofs

The resin-impregnated foam materials of the present invention are further useful as protective coverings and/or therapeutic supports for animal hoofs, such as horse hoofs. Such protective coverings and/or therapeutic supports of the present invention have been used to protect and/or support the sole of a horse hoof, including the soft, recessed, and very uneven area under a horse's hoof known as the "frog area." The resin-impregnated foam materials of the present invention cure in intimate contact with the sole and soft frog area of the horse's hoof and protect the sole and soft frog area from rocks or sticks as the horse walks along. During application, the weight of the horse pushes the resin-impregnated material of the present invention up into the sole and frog area and crushes the resin-impregnated foam into a very thin pad around the rim of the horse hoof. After curing, the rigid material both protects the area under the horse hoof and provides uniform support to the sole of the hoof.

In attempting to address this problem, the prior art has typically applied a rubber sheet between the horse hoof and horseshoe, and then silicone or other caulking material is squirted in between the horse hoof and the rubber sheet so as to fill in the voids therebetween. Again, the resin-impregnated foam materials of the present invention, because of their good conformability, can be used for this purpose without the need for any caulking material to fill in the voids. In this respect, the resin-impregnated foam materials of the present invention conform to the bottom of the horse hoofs so that the voids are substantially filled.

Figure 10A:
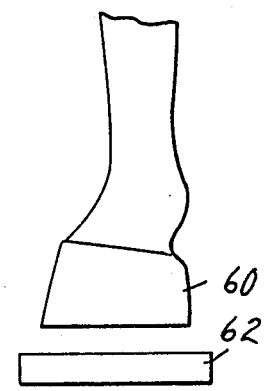
FIG. 10A shows the positioning of a resin-impregnated foam block of the present invention with respect to a horse hoof.
Figure 10B:
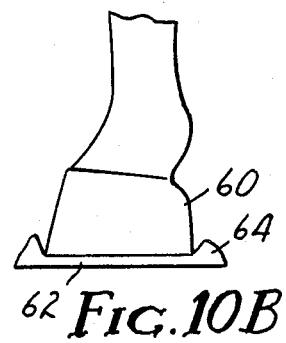
FIG. 10B shows the horse hoof after being pressed down into the resin-impregnated foam block.
Figure 10C:
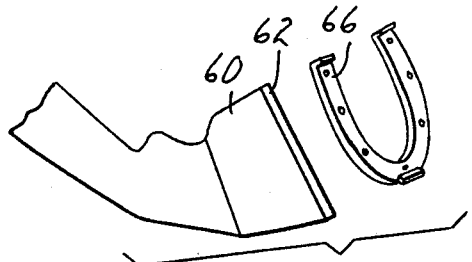
FIG. 10C shows the positioning of the foam block covered horse hoof with respect to a standard horseshoe.
Figure 10D:
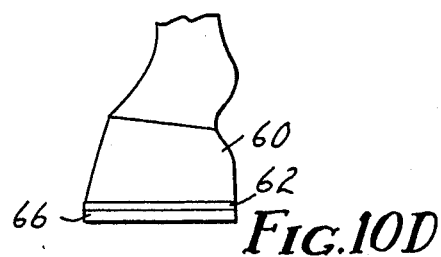
FIG. 10D shows the horseshoe applied to the horse hoof with the resin-impregnated foam block sandwiched therebetween.

Referring now to FIG. 10A, a horse hoof 60 is brought into close proximity with a resin-impregnated foam block 62 within the scope of the present invention which has been activated. As seen in FIG. 10B, the horse hoof 60 is then pressed down onto the resin-impregnated foam block 62, and held there until the resin-impregnated block 62 has completely cured. Because of the conformable nature of foam block 62, the foam block 62 conforms to the contours of the sole and soft frog bottom of hoof 60 and substantially fills any voids therein. Upon curing, any excess foam 64 extending beyond the periphery of hoof 60 is trimmed from around the hoof. Next, as seen in FIG. 10C, a standard horseshoe 66 is brought into proximity with foam pad 62 and applied thereto in normal fashion such as by nails or other securing means to secure the horseshoe 66 to horse hoof 60 with foam pad 62 sandwiched therebetween as shown in FIG. 10D.

Additionally, the resin-impregnated foam materials of the present invention find utility in animal wound dressings. For example, the materials of this invention may be padded with a suitable dressing fabric such as gauze and applied over horse leg wounds.

When the resin-impregnated foam materials of the present invention are used in conjunction with walking heels, supports for orthotic devices, or as protective coverings or therapeutic supports for animal hoofs, or as wound dressings, etc., the exotherm concerns are similar to those which are experienced when such materials of the present invention are used to form splints as outlined herein. In this regard, the previous discussion relating to the various chemical properties of the resin and resin-impregnated foam materials of the splinting application also applies to the other applications of applicants' invention and are incorporated herein by this reference. Hence, the resin impregnated foam materials of the present invention provide materials which can be used safely in a variety of applications without concern for the danger of exothermic burns.

Thus, the aforementioned teachings of the present invention regarding resin-impregnated materials used as splinting materials also apply to the use of such materials in conjunction with walking heels, supports for orthotic devices, as protective coverings or therapeutic supports for animal hoofs, or as wound dressings. However, it is often desirable to use different foam thicknesses in each of these different applications, and thus the thickness of the foam employed is the only major parameter which is variable between the various applications of the present invention. As mentioned, foam thicknesses of between about 5/16 of an inch to about ¾ of an inch are preferred for splinting applications. Foam sheet thicknesses of from about ¾ of an inch to about 1½ inches are preferred in the walking heel applications of the present invention, although foams 3 inches thick or thicker can sometimes be used successfully. When used to stabilize an orthotic such as a foot orthotic, the foam sheet thickness is preferably from about ¼ of an inch to about 1 inch thick. When applied as a pad to an animal hoof, the foam sheet thickness is preferably from about ½ inch to about 1 inch thick. When used as a wound dressing, the foam sheet thickness is preferably from about ¼ inch to about 1 inch thick.

The following are actual examples which were conducted in accordance with the present invention. These examples are given for purposes of illustration only, and should not be deemed in any way to be comprehensive or limiting.

EXAMPLE 6

In this example, a walking heel within the scope of the present invention was prepared. First, foam blocks measuring 4 inches by 6 inches and having a thickness of 1½ inches were cut from the same type of E-150 polyurethane foam used in Example 1. Each foam block was impregnated with a resin in sufficient amount that the resin represented about 90% by weight of the final resin-impregnated foam sheet. The identity and amounts of the various ingredients used to formulate the resin used in this example are set forth below:

| Ingredient | Amount (g) |
| --- | --- |
| Isonate 143L (Upjohn) | 1324.7 |
| PPG-425 (Union Carbide) | 544.2 |
| PPG-1025 (Union Carbide) | 250.4 |
| Benzoyl chloride | 1.62 |
| Pluronic F-38 (BASF Wyandotte) | 101.25 |
| MEMPE catalyst (3M) | 22.5 |
| DB-100 silicone fluid (Dow Corning) | 5.39 |

The resultant polyurethane prepolymer resin had an NCO:OH ratio of about 3:1 and an NCO equivalent weight of about 370 grams of prepolymer per NCO group. The resin components were blended together and coated by hand onto the foam before the resin had substantially reacted so that it was in still a relatively low viscosity state. The coating operation was done under low humidity conditions (less than 10% relative humidity), and the coated foam blocks were stored in heat-sealed foil pouches for further use.

Later, a resin-impregnated foam block so prepared was removed from its foil pouch and activated by dipping in water at room temperature. Excess water was removed by squeezing. The activated resin-impregnated foam block was then placed between the uneven bottom of an orthopedic short leg cast and a plywood plate to which a preformed walking heel had been attached. The curing foam block compressed to fill the uneven space between the bottom of the cast and the mounted, preformed walking heel. The resin-impregnated foam allowed proper orientation of the walking heel with respect to the ground, without the need for additional shimming. The cured foam block provided a very strong bond between the preformed walking heel and the bottom of the cast. Excess foam was then cut away. About 20 minutes after activation of the resin-impregnated foam block, the patient was walking on the newly mounted walking heel. The walking heel assembly proved to be both comfortable for the patient and durable.

EXAMPLE 7

In this example, a walking heel within the scope of the present invention was prepared such that the walking heel was formed from the resin-impregnated foam material itself. First, foam blocks measuring 4 inches by 12 inches and having a thickness of 1½ inches were cut from the same type of E-150 polyurethane foam used in Example 1. Each foam block was impregnated with the resin of Example 6 in sufficient amount that the resin represented about 90% by weight of the final resin-impregnated foam sheet.

The resin was coated by hand onto the foam before the resin had substantially reacted so that it was in still a relatively low viscosity state. The coating operation was done under low humidity conditions (less than 10% relative humidity), and the coated foam blocks were stored in heat-sealed foil pouches for further use.

Later, a resin-impregnated foam block so prepared was removed from its foil pouch and activated by dipping in water at room temperature. Excess water was removed by squeezing. The activated resin-impregnated foam block was then placed between the uneven bottom of an orthopedic short leg cast and a mold (which mold was covered with a thin plastic film) having a curved surface, much like mold 44 shown in FIG. 7B. The patient placed weight on the short leg cast so that the resin-impregnated foam block was compressed between the short leg cast and the mold. After about 4 minutes, the resin-impregnated foam block had cured in the shape of a curved walking surface much like that shown in FIG. 7D, and the mold was removed. Excess foam around the periphery of the cast was trimmed away with a knife. In about 20 minutes after application, the foam had cured to the point that it was capable of bearing the weight of the patient, and the patient walked easily around the room. A thin wear strip of neoprene rubber was then adhesively attached to the bottom of the cured walking heel. The resin-impregnated foam material provided additional strength to the foot area of the walking cast, and the walking heel provided a comfortable, easy to use walking surface for the patient.

EXAMPLE 8

In this example, a support for a foot orthotic within the scope of the present invention was prepared. First, foam blocks were cut from the same type of E-150 polyurethane foam used in Example 1 such that the foam blocks measured 4 inches by 2 inches with a tapered width. In regard to the tapered width, the foam measured about ½ inch thick along one 4 inch side and approximately 1/8 inch thick along the other 4 inch side. Each foam block was impregnated with a resin in sufficient amount that the resin represented about 90% by weight of the final resin-impregnated foam sheet. The identity and amounts of the various ingredients used to formulate the resin used in this example are set forth below:

| Ingredient | Amount (g) |
| --- | --- |
| Isonate 143L | 334.31 |
| PPG-1025 | 373.24 |
| Benzoyl chloride | 0.68 |
| Pluronic F-38 | 30.0 |
| MEMPE catalyst | 7.5 |
| DB-100 silicone fluid | 1.73 |

The resultant polyurethane prepolymer resin had an NCO:OH ratio of about 3:1 and an NCO equivalent weight of about 485 grams of prepolymer per NCO group. The resin components were blended together and coated by hand onto the foam before the resin had substantially reacted so that it was in still a relatively low viscosity state. The coating operation was done under low humidity conditions (less than 10% relative humidity), and the coated blocks were stored in heat-sealed foil pouches for further use.

A roll of Scotchcast® 2 orthopedic casting tape (3M, St. Paul, Minn.) measuring 4 inches wide was removed from its package and folded upon itself to provide a piece of folded tape measuring 4 inches by 12 inches having 3 layers folded upon each other. The folded casting tape was activated by dipping it in water at room temperature, and excess water was removed by squeezing. The activated casting tape was then placed on a piece of foam measuring 8 inches by 14 inches and having a thickness of 1½ inches, which foam had been covered with a thin polyethylene film to protect the foam. The activated casting tape was covered with a piece of ethylene propylene rubber film procured from Clopay Corporation, Cincinnati, Ohio, as Elastoflex P film, to protect the patient's foot. The patient's foot was then pressed down into the curing casting tape. The foam pad allowed the casting tape to conform exactly to the bottom of the patient's foot. After about 4 minutes, the cured casting tape was trimmed to the proper size to form a finished orthotic.

Subsequently, a resin-impregnated foam block prepared in this example was removed from its respective foil pouch and activated by dipping in water at room temperature. Excess water was removed by squeezing. The orthotic prepared in this example was placed under the patient's foot with the activated foam block positioned under the arch of the orthotic. In this regard, the curing foam block was oriented so that the side having the ½ inch thickness was in line with the inside length of the orthotic. A protective layer of Elastoflex P film was placed under the foam block to protect the floor. The patient put weight on the orthotic to compress the foam and attach it to the orthotic. In about 5 minutes, the foam block was found to have cured and bonded securely to the orthotic. The cured foam block provided excellent support for the thin orthotic shell, and required only a minor amount of trimming to match the peripheral contours of the orthotic.

EXAMPLE 9

In this example, a horse hoof pad within the scope of the present invention was prepared. First, circular pieces of foam measuring 8 inches in diameter and having a thickness of ¾ of an inch were cut from the same type of E-150 polyurethane foam used in Example 1. Each piece of foam was impregnated with the resin in sufficient amount that the resin represented about 90% by weight of the final resin-impregnated foam sheet. The identity and amounts of the various ingredients used to formulate the resin used in this example are set forth below:

| Ingredient | Amount (g) |
| --- | --- |
| Isonate 143L | 1324.65 |
| PPG-425 | 544.2 |
| PPG-1025 | 250.4 |
| Benzoyl chloride | 1.62 |
| Pluronic F-38 | 101.25 |
| DB-100 silicone fluid | 5.39 |
| MEMPE catalyst | 22.5 |

The resultant polyurethane prepolymer resin had an NCO:OH ratio of about 3:1 and an NCO equivalent weight of about 365 grams of prepolymer per NCO group. The resin components were blended together and coated by hand onto the circular foam pieces before the resin had substantially reacted so that it was in still a relatively low viscosity state. The coating operation was done under low humidity conditions (less than 10% relative humidity), and the coated circular foam pieces were stored in heat-sealed foil pouches for further use.

Later, a horse hoof pad was formed as follows. First, a horse hoof was prepared for shoeing in the normal fashion. The sole, including the soft frog area of the horse hoof, was cleaned and wiped with isopropyl alcohol. A circular resin-impregnated foam sheet prepared in this example was removed from its foil pouch and activated by dipping in water at room temperature. Excess water was removed by squeezing. The activated resin-impregnated foam sheet was pressed onto the bottom of the raised hoof, and the hoof was then lowered onto the empty pouch which had been placed on the floor. Excess foam was cut away from around the periphery of the horse hoof, and the compressed, conforming pad was allowed to cure for about 5 minutes. A standard horseshoe was then nailed in place over the cured pad. The cured pad conformed exactly to the under portion of the horse hoof and provided a tough, rigid, protective covering for the horse hoof.

The present invention may be embodied in other specific forms without departing from its spirit or essential characteristics. The described embodiments are to be considered in all respects only as illustrative and not restrictive. For example, it will be understood that the resin-impregnated foam materials of the present invention may be used in other applicatons to provide a material which conforms well to the surface of an article and at the same time provides an even, smooth, weight bearing surface, and the present invention is not limited to the illustrative examples included herein.

The scope of the invention is, therefore, indicated by the appended claims rather than by the foregoing description. All changes which come within the meaning and range of equivalency of the claims are to be embraced within their scope.

What is claimed and desired to be secured by United States Letters Patent is:

1. A walking heel for an orthopedic cast, said walking heel comprising:
   an open-celled foam sheet; and
   a curable prepolymer resin impregnated into said open-celled foam sheet, said resin-impregnated foam sheet being packaged as a walking heel;
   wherein upon curing said resin-impregnated foam sheet becomes rigid and weight bearing so as to function as a walking heel.

2. A walking heel as defined in claim 1 wherein said prepolymer resin is a water curable, isocyanate functional, prepolymer resin.

3. A walking heel as defined in claim 2 wherein said isocyanate functional, prepolymer resin is formed by reacting a polyisocyanate with a polyol and wherein the ratio of NCO groups in said polyisocyanate to OH groups in said polyol is between about 2 to 1 and about 3.5 to 1, said prepolymer resin having an NCO equivalent weight of from about 350 to about 1000 grams of prepolymer resin per NCO group.

4. A walking heel as defined in claim 3 wherein said prepolymer resin is formed by reacting said polyisocyanate with said polyol while said polyisocyanate and said polyol are inside said open-celled foam sheet.

5. A walking heel as defined in claim 1 wherein said open-celled foam sheet has from about 30 to about 100 pores per inch.

6. A walking heel as defined in claim 1 wherein said open-celled foam sheet has a density of from about 1 to about 4.5 lbs/ft$^3$.

7. A walking heel as defined in claim 1 wherein said prepolymer resin comprises from about 70% to about 95% by weight of said resin-impregnated foam sheet.

8. A walking heel as defined in claim 3 wherein, after reaction of said polyisocyanate and said polyol, said prepolymer resin has a viscosity of about 75,000 centipoise or greater.

9. A walking heel as defined in claim 3 wherein said prepolymer resin has an NCO equivalent weight of from about 370 to about 600 grams of prepolymer resin per NCO group.

10. A walking heel as defined in claim 1 wherein upon curing said prepolymer resin, a temperature of about 48° C. or less is felt by an animal to which said walking heel is applied.

11. A walking heel as defined in claim 1 wherein said resin further comprises a tack reducing agent.

12. A walking heel as defined in claim 1 wherein said prepolymer resin further comprises a catalyst and wherein said resin-impregnated foam sheet is sealed within a water vapor impermeable package.

13. A walking heel as defined in claim 1 wherein said walking heel further comprises a rubber sheet applied thereto to serve as a wear surface.

14. A support for an orthotic device, said support comprising:
   an open-celled foam sheet; and
   a curable prepolymer resin impregnated into said open-celled foam sheet, said resin-impregnated foam sheet being packaged as a support for an orthotic device;
   wherein upon curing said resin-impregnated foam sheet becomes rigid and weight bearing so as to function as an orthotic device support.

15. A support for an orthotic device as defined in claim 14 wherein said prepolymer resin is a water curable, isocyanate functional, prepolymer resin.

16. A support for an orthotic device as defined in claim 15 wherein said isocyanate functional, prepolymer resin is formed by reacting a polyisocyanate with a polyol and wherein the ratio of NCO groups in said polyisocyanate to OH groups in said polyol is between about 2 to 1 and about 3.5 to 1, said prepolymer resin having an NCO equivalent weight of from about 350 to about 1000 grams of prepolymer resin per NCO group.

17. A support for an animal hoof, said support comprising:
   an open-celled foam sheet; and
   a curable prepolymer resin impregnated into said open-celled foam sheet, said resin-impregnated foam sheet being packaged as a support for an animal hoof;
   wherein upon curing said resin-impregnated foam sheet becomes rigid and weight bearing so as to function as an animal hoof support.

18. A support for an animal hoof as defined in claim 17 wherein said prepolymer resin is a water curable, isocyanate functional, prepolymer resin.

19. A support for an animal hoof as defined in claim 18 wherein said isocyanate functional, prepolymer resin is formed by reacting a polyisocyanate with a polyol and wherein the ratio of NCO groups in said polyisocyanate to OH groups in said polyol is between about 2 to 1 and about 3.5 to 1, said prepolymer resin having an NCO equivalent weight of from about 350 to about 1000 grams of prepolymer resin per NCO group.

20. A foot cast/walking heel assembly comprising:
   a foot cast;
   a walking heel; and
   a laminating layer joining said foot cast to said walking heel, said laminating layer comprising an open-celled foam sheet and a curable prepolymer resin impregnated into said open-celled foam sheet, wherein upon curing said resin-impregnated foam sheet becomes rigid and weight bearing.

21. A foot cast/walking heel assembly as defined in claim 20 wherein said walking heel comprises a flat board to which is secured a rubber walking member.

22. A foot cast/walking heel assembly as defined in claim 20 wherein said prepolymer resin is a water curable, isocyanate functional, prepolymer resin.

23. A foot cast/walking heel assembly as defined in claim 22 wherein said isocyanate functional, prepolymer resin is formed by reacting a polyisocyanate with a polyol and wherein the ratio of NCO groups in said polyisocyanate to OH groups in said polyol is between about 2 to 1 and about 3.5 to 1, said prepolymer resin having an NCO equivalent weight of from about 350 to about 1000 grams of prepolymer resin per NCO group.

24. A foot cast/walking heel assembly comprising:
a foot cast; and
a walking heel applied to said foot cast, said walking heel comprising an open-celled foam sheet and a curable prepolymer resin impregnated into said open-celled foam sheet, wherein upon curing said resin-impregnated foam sheet becomes rigid and weight bearing.

25. A foot cast/walking heel assembly as defined in claim 24 wherein said prepolymer resin is a water curable, isocyanate functional, prepolymer resin.

26. A foot cast/walking heel assembly as defined in claim 25 wherein said isocyanate functional, prepolymer resin is formed by reacting a polyisocyanate with a polyol and wherein the ratio of NCO groups in said polyisocyanate to OH groups in said polyol is between about 2 to 1 and about 3.5 to 1, said prepolymer resin having an NCO equivalent weight of from about 350 to about 1000 grams of prepolymer resin per NCO group.

27. An orthotic device comprising:
an orthotic shaped to the contours of a body part to which it is to be applied; and
a support layer laminated to said orthotic so as to provide a weight bearing surface therefor, said support layer comprising an open-celled foam sheet and a curable prepolymer resin impregnated into said open-celled foam sheet, wherein upon curing said resin-impregnated foam sheet becomes rigid and weight bearing.

28. An orthotic device as defined in claim 27 wherein said prepolymer resin is a water curable, isocyanate functional, prepolymer resin.

29. An orthotic device as defined in claim 28 wherein said isocyanate functional, prepolymer resin is formed by reacting a polyisocyanate with a polyol and wherein the ratio of NCO groups in said polyisocyanate to OH groups in said polyol is between about 2 to 1 and about 3.5 to 1, said prepolymer resin having an NCO equivalent weight of from about 350 to about 1000 grams of prepolymer resin per NCO group.

30. An improved horseshoe assembly, comprising:
a horseshoe; and
a protective layer applied between said horseshoe and a horse's hoof, said protective layer comprising an open-celled foam sheet and a curable prepolymer resin impregnated into said open-celled foam sheet, wherein upon curing said resin-impregnated foam sheet becomes rigid and weight bearing.

31. An improved horseshoe assembly as defined in claim 30 wherein said prepolymer resin is a water curable, isocyanate functional, prepolymer resin.

32. An improved horseshoe assembly as defined in claim 31 wherein said isocyanate functional, prepolymer resin is formed by reacting a polyisocyanate with a polyol and wherein the ratio of NCO groups in said polyisocyanate to OH groups in said polyol is between about 2 to 1 and about 3.5 to 1, said prepolymer resin having an NCO equivalent weight of from about 350 to about 1000 grams of prepolymer resin per NCO group.

33. A laminating material for mounting a walking heel to an orthopedic cast, said laminating material comprising:
an open-celled foam sheet; and
a curable prepolymer resin impregnated into said open-celled foam sheet, said resin-impregnated foam sheet being packaged as a laminating material for mounting a walking heel to an orthopedic cast;
wherein upon curing said resin-impregnated foam sheet becomes rigid and weight bearing so as to provide adequate support between said walking heel and said orthopedic cast.

* * * * *

UNITED STATES PATENT AND TRADEMARK OFFICE
CERTIFICATE OF CORRECTION

PATENT NO.  : 4,888,225

DATED       : December 19, 1989

INVENTOR(S) : Timothy C. Sandvig et al.

It is certified that error appears in the above-identified patent and that said Letters Patent is hereby corrected as shown below:

Col. 4, line 33, "an" should be --and--.

Col. 11, line 3, after "in" insert --commonly--.

Col. 12, line 68, after "tailored", insert --to the--.

Col. 15, line 10, "acceptions" should be --exceptions--.

Col. 23, line 23, "applicatons" should be --applications--.

Signed and Sealed this

Twenty-ninth Day of January, 1991

*Attest:*

HARRY F. MANBECK, JR.

*Attesting Officer*  *Commissioner of Patents and Trademarks*